United States Patent [19]
Varshavsky et al.

[11] Patent Number: 5,763,212
[45] Date of Patent: Jun. 9, 1998

[54] INHIBITING DEGRADATION OF A DEGRON-BEARING PROTEIN

[75] Inventors: Alexander Varshavsky, La Canada Flintridge; Jennifer Johnston, Altadena, both of Calif.

[73] Assignee: California Institute of Technology, Pasadena, Calif.

[21] Appl. No.: 417,791

[22] Filed: Apr. 6, 1995

Related U.S. Application Data

[63] Continuation-in-part of Ser. No. 192,479, Feb. 4, 1994, Pat. No. 5,538,862.

[51] Int. Cl.$^6$ ............................... C12P 21/02; C12N 1/21; C12N 5/10
[52] U.S. Cl. .................. 435/69.1; 435/69.7; 435/252.3; 435/325
[58] Field of Search ................................. 435/69.1, 69.7, 435/240.2, 252.3, 325; 514/2, 12; 536/22.1, 23.1, 23.2, 23.4, 23.5

[56] References Cited

U.S. PATENT DOCUMENTS

| | | | |
|---|---|---|---|
| 5,093,242 | 3/1992 | Bachmair et al. | 435/69.7 |
| 5,122,463 | 6/1992 | Varshavsky et al. | 435/69.7 |
| 5,132,213 | 7/1992 | Bachmair et al. | 435/69.7 |
| 5,196,321 | 3/1993 | Bachmair et al. | 435/69.7 |
| 5,212,058 | 5/1993 | Baker et al. | 435/252.33 |

OTHER PUBLICATIONS

Pongor, S. Methods in Enzymology, 154:450–473, 1987.
Alberts et al. Molecular Biology of the Cell, Garland Publishing, NY, pp. 219–221, 1994.
Varshavsky, Alexander, "The N–End Rule", *Cell* 69: 725 (1992).
Matthews et al., *J. Biol. Chem.* 260: 392 (1985).

*Primary Examiner*—Robert A. Wax
*Assistant Examiner*—Kawai Lau
*Attorney, Agent, or Firm*—Kevin M. Farrell

[57] ABSTRACT

Disclosed herein is a heat-inducible N-degron module. A heat-inducible N-degron module is a protein or peptide bearing a destabilizing N-terminal amino acid residue which becomes a substrate of the N-end rule pathway only at a temperature high enough to result in at least partial unfolding of the protein. At this elevated (nonpermissive) temperature, the heat-inducible N-degron module (and any protein or peptide attached at its C-terminus) is rapidly degraded in a cell in which the N-end rule pathway is operative. Also disclosed are DNA and protein fusion constructs, methods for screening for additional heat-inducible N-degron modules and methods for using the disclosed heat-inducible N-degron modules. Also disclosed are methods for inhibiting the degradation of a protein bearing an N-degron in which a low molecular mass, cell penetrating ligand is prebound to the protein.

4 Claims, 4 Drawing Sheets

| t (°C) | Half-life in S. cerevisiae | | Phenotypes with Ura3 as domain 3 | | Phenotypes with Cdc28 as domain 3 | |
|---|---|---|---|---|---|---|
| | UBR1 | ubr1Δ | UBR1 | ubr1Δ | UBR1 | ubr1Δ |
| 23°C | deubiquitination (cotranslational) | | | | | |
| 23°C | long | long | Ura⁺ | Ura⁺ | growth | growth |
| 37°C | short | long | Ura⁻ | Ura⁺ | arrest | growth |

FIG. 1

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 579 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..579

( x i ) SEQUENCE DESCRIPTION: SEQ ID NO:1:

```
AGG  CAC  GGA  TCC  GGC  ATC  ATG  GTT  CGA  CCA  TTG  AAC  TGC  ATC  GTC  GCC         48
Arg  His  Gly  Ser  Gly  Ile  Met  Val  Arg  Pro  Leu  Asn  Cys  Ile  Val  Ala
  1              5                       10                       15

GTG  TCC  CAA  AAT  ATG  GGG  ATT  GGC  AAG  AAC  GGA  GAC  CTA  CCC  TGG  CCT         96
Val  Ser  Gln  Asn  Met  Gly  Ile  Gly  Lys  Asn  Gly  Asp  Leu  Pro  Trp  Pro
               20                       25                       30

CCG  CTC  AGG  AAC  GAG  TTC  AAG  TAC  TTC  CAA  AGA  ATG  ACC  ACA  ACC  TCT        144
Pro  Leu  Arg  Asn  Glu  Phe  Lys  Tyr  Phe  Gln  Arg  Met  Thr  Thr  Thr  Ser
          35                       40                       45

TCA  GAG  GAA  GGT  AAA  CAG  AAT  CTG  GTG  ATT  ATG  GGT  AGG  AAA  ACC  TGG        192
Ser  Glu  Glu  Gly  Lys  Gln  Asn  Leu  Val  Ile  Met  Gly  Arg  Lys  Thr  Trp
      50                       55                       60

TTC  TCC  ATT  CCT  GAG  AAG  AAT  CGA  CTT  TTA  AAG  GAC  AGA  ATT  AAT  ATA        240
Phe  Ser  Ile  Pro  Glu  Lys  Asn  Arg  Leu  Leu  Lys  Asp  Arg  Ile  Asn  Ile
 65                       70                       75                       80

GTT  CTC  AGT  AGA  GAA  CTC  AAA  GAA  CCA  CCA  CGA  GGA  GCT  CAT  TTT  CTT        288
Val  Leu  Ser  Arg  Glu  Leu  Lys  Glu  Pro  Pro  Arg  Gly  Ala  His  Phe  Leu
                85                       90                       95

GCC  AAA  AGT  TTG  GAT  GAT  GCC  TTA  AGA  CTT  ATT  GAA  CAA  CCG  GAA  TTG        336
Ala  Lys  Ser  Leu  Asp  Asp  Ala  Leu  Arg  Leu  Ile  Glu  Gln  Pro  Glu  Leu
                    100                      105                      110

GCA  AGT  AAA  GTA  GAC  ATG  GTT  TGG  ATA  GTC  GGA  GGC  AGT  TCT  GTT  TAC        384
Ala  Ser  Lys  Val  Asp  Met  Val  Trp  Ile  Val  Gly  Gly  Ser  Ser  Val  Tyr
              115                      120                      125
```

| | | | | | | | | | | | | | | | | |
|---|---|---|---|---|---|---|---|---|---|---|---|---|---|---|---|---|
| CAG | GAA | GCC | ATG | AAT | CAA | CCA | GGC | CAC | CTC | AGA | CTC | TTT | GTG | ACA | AGG | 432 |
| Gln | Glu | Ala | Met | Asn | Gln | Pro | Gly | His | Leu | Arg | Leu | Phe | Val | Thr | Arg | |
| | 130 | | | | 135 | | | | | 140 | | | | | | |
| ATC | ATG | CAG | GAA | TTT | GAA | AGT | GAC | ACG | TTT | TTC | CCA | GAA | ATT | GAT | TTG | 480 |
| Ile | Met | Gln | Glu | Phe | Glu | Ser | Asp | Thr | Phe | Phe | Pro | Glu | Ile | Asp | Leu | |
| 145 | | | | | 150 | | | | | 155 | | | | | 160 | |
| GGG | AAA | TAT | AAA | CTT | CTC | CCA | GAA | TAC | CCA | GGC | GTC | CTC | TCT | GAG | GTC | 528 |
| Gly | Lys | Tyr | Lys | Leu | Leu | Pro | Glu | Tyr | Pro | Gly | Val | Leu | Ser | Glu | Val | |
| | | | | 165 | | | | | 170 | | | | | 175 | | |
| CAG | GAG | GAA | AAA | GGC | ATC | AAG | TAT | AAG | TTT | GAA | GTC | TAC | GAG | AAG | AAA | 576 |
| Gln | Glu | Glu | Lys | Gly | Ile | Lys | Tyr | Lys | Phe | Glu | Val | Tyr | Glu | Lys | Lys | |
| | | | 180 | | | | | 185 | | | | | 190 | | | |
| GAC | | | | | | | | | | | | | | | | 579 |
| Asp | | | | | | | | | | | | | | | | |

(2) INFORMATION FOR SEQ ID NO:2:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Arg | His | Gly | Ser | Gly | Ile | Met | Val | Arg | Pro | Leu | Asn | Cys | Ile | Val | Ala |
| 1 | | | | 5 | | | | | 10 | | | | | 15 | |
| Val | Ser | Gln | Asn | Met | Gly | Ile | Gly | Lys | Asn | Gly | Asp | Leu | Pro | Trp | Pro |
| | | | 20 | | | | | 25 | | | | | 30 | | |
| Pro | Leu | Arg | Asn | Glu | Phe | Lys | Tyr | Phe | Gln | Arg | Met | Thr | Thr | Thr | Ser |
| | | 35 | | | | | 40 | | | | | 45 | | | |
| Ser | Glu | Glu | Gly | Lys | Gln | Asn | Leu | Val | Ile | Met | Gly | Arg | Lys | Thr | Trp |
| | 50 | | | | | 55 | | | | | 60 | | | | |
| Phe | Ser | Ile | Pro | Glu | Lys | Asn | Arg | Leu | Leu | Lys | Asp | Arg | Ile | Asn | Ile |
| 65 | | | | | 70 | | | | | 75 | | | | | 80 |
| Val | Leu | Ser | Arg | Glu | Leu | Lys | Glu | Pro | Pro | Arg | Gly | Ala | His | Phe | Leu |
| | | | | 85 | | | | | 90 | | | | | 95 | |
| Ala | Lys | Ser | Leu | Asp | Asp | Ala | Leu | Arg | Leu | Ile | Glu | Gln | Pro | Glu | Leu |
| | | | 100 | | | | | 105 | | | | | 110 | | |
| Ala | Ser | Lys | Val | Asp | Met | Val | Trp | Ile | Val | Gly | Gly | Ser | Ser | Val | Tyr |
| | | 115 | | | | | 120 | | | | | 125 | | | |
| Gln | Glu | Ala | Met | Asn | Gln | Pro | Gly | His | Leu | Arg | Leu | Phe | Val | Thr | Arg |
| | 130 | | | | | 135 | | | | | 140 | | | | |
| Ile | Met | Gln | Glu | Phe | Glu | Ser | Asp | Thr | Phe | Phe | Pro | Glu | Ile | Asp | Leu |
| 145 | | | | | 150 | | | | | 155 | | | | | 160 |
| Gly | Lys | Tyr | Lys | Leu | Leu | Pro | Glu | Tyr | Pro | Gly | Val | Leu | Ser | Glu | Val |
| | | | | 165 | | | | | 170 | | | | | 175 | |
| Gln | Glu | Glu | Lys | Gly | Ile | Lys | Tyr | Lys | Phe | Glu | Val | Tyr | Glu | Lys | Lys |
| | | | 180 | | | | | 185 | | | | | 190 | | |
| Asp | | | | | | | | | | | | | | | |

INHIBITING DEGRADATION OF A DEGRON-BEARING PROTEIN

RELATED APPLICATIONS

The present application is a continuation-in-part of U.S. application Ser. No. 08/192,479, filed Feb. 4, 1994 now U.S. Pat. No. 5,538,862.

GOVERNMENT SUPPORT

Experimental work disclosed herein was supported by a grant from the National Institutes of Health and the government has certain rights in the invention.

BACKGROUND OF THE INVENTION

The surface of any protein bears a number of peptide bonds—potential cleavage sites for proteases. The rate of peptide bond cleavage by even a relatively nonspecific protease depends on conformational flexibility of the motif that the protease recognizes. For example, only some of the potential cleavage sites on the surface of a globular protein are cleaved efficiently by the bacterial metalloendoprotease thermolysin, and these preferred cleavage sites are located in exposed segments of the polypeptide chain that have the highest spatial mobility.

Thus, even if a motif recognized by a protease is present on the surface of a protein, conformational rigidity of this potential degron may preclude its efficient utilization by the protease. Conversely, a conformationally destabilized protein may acquire degrons that are masked in an unperturbed version of the protein. This can happen not only through conformational relaxation of a previously rigid (and therefore cryptic) surface degron, but also through exposure of degrons in previously buried regions of the protein. The mechanistic connection between segmental mobility of a polypeptide chain and its susceptibility to proteolysis stems from a scarcity of local chain conformations that can lend themselves to an optimal transition-state intermediate without a conformational adjustment.

Dynamic aspects of a substrate's conformation are likely to play a major role in the functioning of intracellular proteolytic systems such as those that involve the multisubunit, multicatalytic protease called the proteasome. A salient feature of these ATP-dependent systems is their processivity: once the degradation of a protein begins, it proceeds to completion. Thus, a proteasome-mediated system should be able to perturb the conformation of a globular protein substrate before or during its processive degradation by the proteasome. The "conformational" problem to be solved by the proteasome is analogous to the problem faced by a protein translocation system: components of a transmembrane channel must unfold a protein before or during its "threading" across membrane, except that in this case the protein is transported rather than destroyed. The ability to specifically intervene in the degradation process by interfering with substrate recognition/processing would represent a major technical advance.

SUMMARY OF THE INVENTION

The subject invention relates, in one aspect, to a heat-inducible N-degron module and to DNA encoding same. In a preferred embodiment, the DNA encoding the heat-inducible N-degron module hybridizes to the DNA represented in SEQ ID NO: 1, or its complement, under stringent hybridization conditions.

The DNA encoding the heat-inducible N-degron module can be linked covalently at its 3' end to the 5' end of a DNA sequence encoding a protein (or peptide) of interest. When expressed in a cell in which the N-end rule of protein degradation is operative, the heat-inducible N-degron module, and any protein (or peptide) linked to the C-terminus of the heat-inducible N-degron module, are rapidly degraded by enzymatic components of the N-end rule proteolytic pathway.

A specific heat-inducible N-degron module is disclosed herein. In addition, methods for the identification of additional functional heat-inducible N-degron modules are also disclosed. Such methods are useful for the isolation of heat-inducible N-degron modules using simple screening processes. Finally, it is disclosed that a low molecular weight ligand that binds to a heat-inducible N-degron can interfere with its activation by heat, thereby allowing modulation of the activity of the N-degron by agents other than temperature.

In another aspect, the subject invention relates to methods for inhibiting the degradation of a protein bearing an N-degron. Such inhibition is accomplished, for example, by prebinding a protein with a low molecular mass ligand which binds to the protein with high affinity (e.g., a ligand having a dissociation constant of $10^{-8}$ or lower).

BRIEF DESCRIPTION OF THE DRAWING

FIG. 1 is a diagram representing phenotypic characteristics of a fusion protein comprising a heat-inducible N-degron module linked at its C-terminus to the N-terminus of a protein of interest.

DETAILED DESCRIPTION OF THE INVENTION

Figure 2:
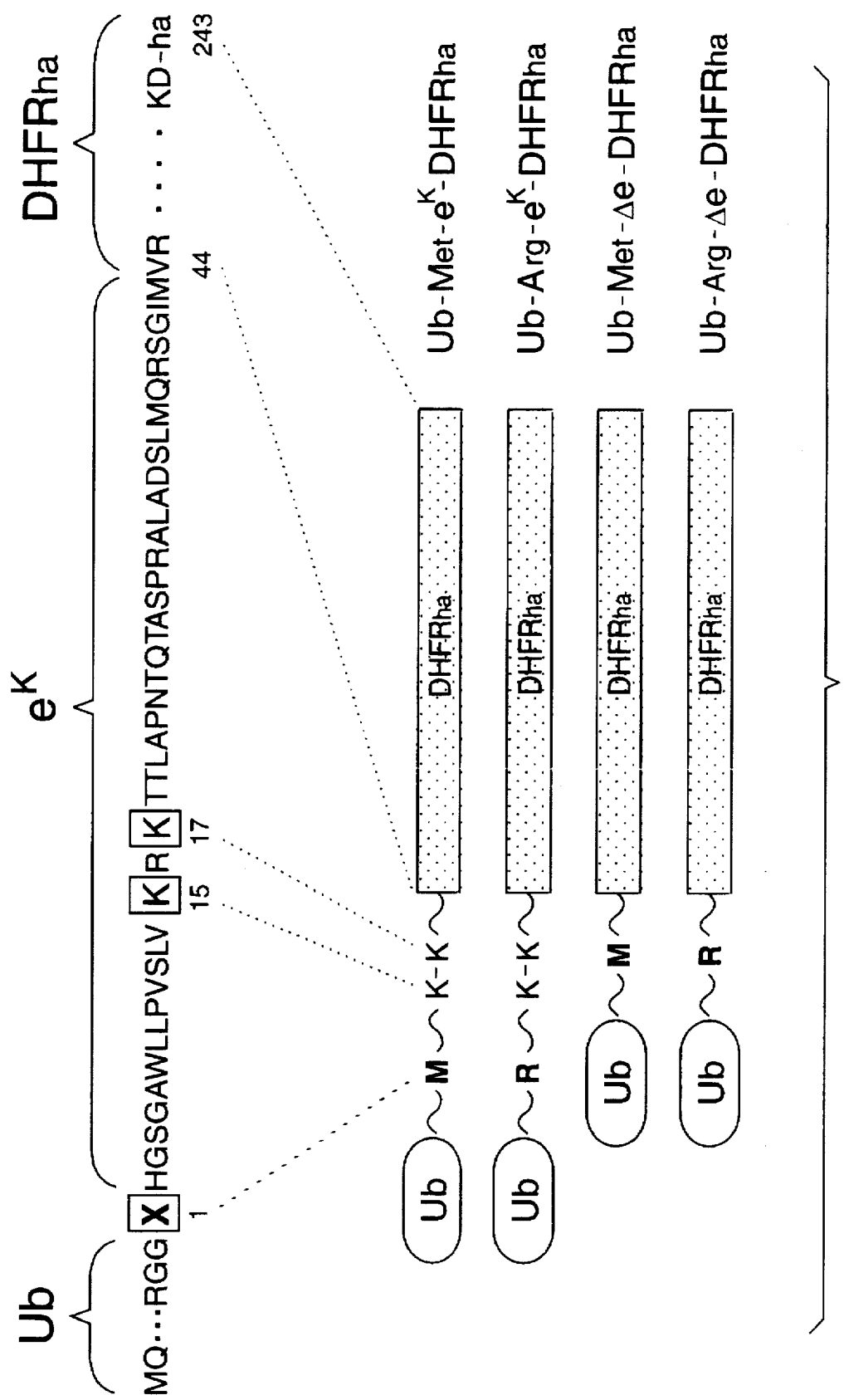
FIG. 2 is a diagram representing test proteins utilized in the experiments described herein. DHFRha is mouse dihydrofolate reductase whose C-terminus was extended with a 14-residue sequence containing the hemagglutinin (ha) epitope. The 43-residue region (derived from *E. coli* Lac repressor) between the Ub and DHFRha moieties in Ub-Met-$e^K$-DHFRha and UB-Arg-$e^K$-DHFRha is denoted by $e^K$ [extension (e) containing lysine (K)] (Bachmair and Varshavsky, *Cell* 56: 1019 (1989); Johnson et al., *Nature* 346: 287 (1990)). The residues are numbered from a residue X at the Ub-$e^K$ junction to the last residue of ha epitope in Ub-X-$e^K$-DHFRha.

The N-degron is an intracellular degradation signal whose essential determinant is a specific ("destabilizing") N-terminal amino acid residue of a substrate protein. A set of N-degrons containing different destabilizing residues is manifested as the N-end rule, which relates the in vivo half-life of a protein to the identity of its N-terminal residue. The fundamental principles of the N-end rule, and the proteolytic pathway that implements it, are well-established in the literature (see, e.g., Bachmair et al., Science 234: 179 (1986); Varshavsky, Cell 69: 725 (1992)), and are the subject of several issued patents. Specifically, aspects of the N-end rule which are relevant to the subject invention are patented in U.S. Pat. Nos.: 5,132,213, 5,093,242 and 5,196,321, the disclosures of which are incorporated herein by reference.

In eukaryotes, the N-degron comprises at least two determinants: a destabilizing N-terminal residue and a specific internal lysine residue (or residues). The latter is the site of attachment of a multiubiquitin chain, whose formation is required for the degradation of at least some N-end rule substrates. Ubiquitin is a protein whose covalent conjugation to other proteins plays a role in a number of cellular processes, primarily through routes that involve protein degradation.

In a stochastic view of the N-degron, each internal lysine of a protein bearing a destabilizing N-terminal residue can be assigned a probability of being utilized as a multiubiquitination site, depending on time-averaged spatial location, orientation and mobility of the lysine. For some, and often for all of the Lys residues in a potential N-end rule substrate, this probability would be infinitesimal because of the lysine's lack of mobility and/or its distance from a destabilizing N-terminal residue.

In one aspect, the present invention is based on the discovery that it is possible to construct a thermolabile protein bearing a destabilizing N-terminal residue in such a way that the protein becomes a substrate of the N-end rule pathway only at a temperature high enough to result in at least partial unfolding of the protein. This unfolding activates a previously cryptic N-degron in the protein by increasing exposure of its (destabilizing) N-terminal residue, by increasing mobilities of its internal Lys residues, or because of both effects at once. Since proteolysis by the N-end rule pathway is highly processive, any protein of interest can be made short-lived at a high (nonpermissive) but not at a low (permissive) temperature by expressing it as a fusion to the thus engineered thermolabile protein, with the latter serving as a portable, heat-inducible N-degron module.

The heat-inducible N-degron module can be any protein or peptide bearing a destabilizing N-terminal residue which becomes a substrate of the N-end rule pathway only at a temperature high enough to be useful as a nonpermissive temperature. In the Exemplification section which follows, an example of such a heat-inducible N-degron module is provided. More specifically, the experiments described herein disclose a ts allele of the 21-kd mouse dihydrofolate reductase protein, in which the wild-type N-terminal Val is replaced by Arg.

The experimental work disclosed herein demonstrates that this ts allele functions as a heat-inducible N-degron module. More specifically, when this heat-inducible N-degron module is fused at its C-terminus to the N-terminus of a protein (or peptide) of interest, the protein (or peptide) of interest also becomes short-lived at the nonpermissive temperature due to the highly processive nature of the N-end rule pathway. Throughout this document, the use of the expression "protein of interest" specifically includes a peptide of interest. Processivity, as used in this context, is defined as the ability of a pathway to complete the initially started degradation of a protein, resulting in protein fragments whose sizes do not significantly exceed those of small peptides (e.g., less than about 20 amino acid residues). This ability is well-established for ubiquitin-dependent proteolytic pathways, and in particular for the N-end rule pathway. It is indicated in particular by the total disappearance of various protein fusions degraded by the N-end rule pathway (see e.g., Hershko, J. Biol. Chem. 263: 15237 (1988); Rechsteiner, Cell 66: 615 (1991); and Varshavsky, Cell 69, 725 (1992)).

The DNA sequence of the ts allele of the 21-kd mouse dihydrofolate reductase protein is set forth in SEQ ID NO: 1. The amino acid residues encoded by this DNA sequence are represented in SEQ ID NOS: 1 and 2. The scope of the invention encompasses any heat-inducible N-degron module which is encoded by a DNA sequence which hybridizes to the DNA sequence of SEQ ID NO: 1, or the complement thereof, under stringent hybridization conditions. Stringent hybridization conditions, as used herein, refer to hybridization in which the DNA molecule represented in SEQ ID NO: 1 is fixed to a solid support and a second DNA molecule to be tested for the ability to hybridize to the DNA of SEQ ID NO: 1 is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.).

Identification of additional heat-inducible N-degron modules requires exclusively straightforward experimental procedures, such as those described in the Exemplification section, which follows. More specifically, in the experiments described below, a nucleic acid construct encoding Ub-Arg-DHFR-ha-Ura3 is described. The fusion protein encoded by this construct is carried on a plasmid which also carries a gene for a selectable marker, and has several features which facilitate the identification of a heat-inducible N-degron module. The N-terminal ubiquitin moiety is included as a transient moiety specifying a cleavage site in the encoded fusion protein between the Ub and Arg-DHFR moieties. Linear fusions of ubiquitin have been demonstrated to be efficiently cleaved between the C-terminal glycine and the N-terminal amino acid residue of the ubiquitin fusion partner (see, e.g., Bachmair et al., Science 234: 179 (1986); Bachmair and Varshavsky, Cell 56: 1019 (1989)). This specific cleavage is effected by a ubiquitin-specific protease activity which has been identified in all eukaryotes examined.

Arg-DHFR is a variant of the 21-kd mouse dihydrofolate reductase in which the wild-type N-terminal Val is replaced by Arg. Arg is a destabilizing residue according to the N-end rule, in that exposure of Arg at the N-terminus of a protein should, if other conditions are met as well, transform a relatively stable (long-lived) protein (such as DHFR or any other protein) to a less stable (more short-lived) protein. The "ha" portion is a 14-residue domain containing an ha epitope. The ha epitope facilitates immunoprecipitation of the Arg-DHFR-ha-Ura3 fusion with a monoclonal anti-ha antibody. The S. cerevisiae Ura3 domain of the fusion protein made possible selections for or against the presence of the fusion protein in cells, while also serving as a test protein.

It will be recognized that individual components of the Arg-DHFR-ha-Ura3 fusion protein can be replaced by functional homologs without compromising the value of the fusion protein for use in a method for identifying a heat-inducible N-degron module. For example, Ura 3 domain can be replaced with another selectable marker domain, Similarly, the ha epitope can be replaced by another immunological tag which facilitates immunoprecipitation of the fusion protein.

To identify additional heat-inducible N-degron modules, a modified protein or peptide moiety other than DHFR can be substituted for Arg-DHFR in the Arg-DHFR-ha-Ura3 fusion protein described above. For example, consider a protein designated "Protein X" (pX). A modified pX bearing a destabilizing N-terminal amino acid residue (e.g., Arg-pX) can be substituted for Arg-DHFR in the fusion construct described in the preceding paragraph. As described herein, this is achieved by placing the Ub moiety in front of Arg-pX within a fusion; the cotranslational cleavage of the Ub moiety at the Ub-Arg junction in vivo will then yield a protein bearing Arg-pX at its N-terminus.

The DNA encoding the Ub-Arg-pX-ha-Ura3 moiety can then be treated with a mutagen. In a ts mutant, the gene product is preferably not too dramatically altered. Therefore, it is preferable to employ mutagens characterized by a tendency to produce missense mutations rather than mutagens which tend to induce more extensive genetic lesions such as deletions. The experiments disclosed herein demonstrate that hydroxylamine is an appropriate mutagen. In addition, a variety of other known mutagens including, for example, N-methyl-N'-nitro-N-nitrosoguanidine (NG), nitrous acid (NA), ethylmethane sulfonate (EMS), and ultraviolet light are known to be useful for the generation of ts mutants (see e.g., Pringle, in *Methods in Cell Biology*, Academic Press, New York, Prescott, ed., 233–271 (1975)). The listing of appropriate mutagens provided herein is meant to provide examples of useful mutagens and is not meant to be comprehensive in the listing of useful mutagens.

The resulting DNA, carried in an appropriate plasmid, is then used to transform cells (e.g., *E. coli* MC1066 cells) to ampicillin resistance with the selection being carried out at 37° C. Transformants are then replica-plated, for example, onto M9 plates containing amp, Trp and Leu, and lacking uracil. Under this selection scheme, the yeast URA3 gene complements the Ura$^-$ phenotype of *E. coli* pyrF mutants. This *E. coli* screen will eliminate mutant plasmids that do not express a functional Ura3 moiety of Ub-Arg-pX-ha-Ura3 at 37° C.

Appropriate plasmid constructs which express a functional Ura3 moiety of Ub-Arg-pX-ha-Ura3 at 37° C. are then screened for the ability to confer a ts Ura$^+$ phenotype whose ts aspect requires the N-end rule pathway. This is accomplished, for example, by introducing such plasmids into *S. cerevisiae* YPH500 (ura3), with transformants selected at 23° C. on SD(-Ura) plates containing 0.1 mM CuSO$_4$. Resulting colonies are replica-plated onto plates appropriate for selection. For example, the resulting colonies can be replica-plated onto SD plates lacking His and containing 5-fluoroorotic acid (FOA) and uracil. The inclusion of FOA serves as a selection against cells expressing Ura3 (Boeke et al., *Mol. Gen. Genet.* 197, 345 (1984)). The FOA plates are then incubated at 37° C. to select against cells that could yield a functional Ura3 at 37° C. After several rounds of the FOA-mediated selection against cells that are Ura$^+$ at 37° C., the ts URA$^+$ phenotype of surviving cell clones can be verified by replica-plating them onto SD(-Ura, -His) plates at 37° C. Plasmids from cells passing these screens are introduced into cells such as the YPH500-derived strain JD15 (described in detail below), with transformants selected on SD(-Ura) plates at 37° C. This step narrows the selection to plasmids having the ability to confer the ts Ura$^+$ phenotype only in the presence of the N-end rule pathway. Conventional sequencing techniques are then used to confirm that the mutation responsible for the desired phenotype is present within the pX domain of the fusion protein. Upon confirmation of this, the mutant Arg-pX moiety has been identified as a heat-inducible N-degron module.

DNA encoding a heat-inducible N-degron module of the type described above can be linked at its 3' end to the 5' end of DNA encoding a protein or peptide of interest, yielding a desired gene fusion construct. The gene fusion, together with any regulatory sequences required for expression, is introduced into cells using conventional techniques. The cells into which the gene fusion is introduced can be either cells grown in culture, or differentiated tissue cells in a whole organism. It will be recognized that these cells should also lack a functioning allele of the gene whose ts mutation is being sought. This can be accomplished, for example, through the use of targeted mutagenesis techniques which are well known in the art. This gene fusion construct is then expressed to produce a protein fusion in which the heat-inducible N-degron module is joined covalently at its C-terminus to the N-terminus of the protein or peptide of interest.

Provided that the cell in which the gene fusion construct is expressed is a cell in which the N-end rule degradation pathway is operative (e.g., any eukaryotic cell), the metabolic fate of the protein or peptide of interest in the fusion protein will be determined by the presence of the heat-inducible N-degron module. Due to the highly processive nature of the N-end rule degradation pathway, the recognition of a destabilizing N-terminal amino acid residue by the recognition component of the pathway seals the fate of the protein fusion. Specifically, at nonpermissive temperatures, the N-terminal residue will be recognized by the recognition component of the N-end rule degradation pathway, and the entire fusion protein will be rapidly degraded. This typically results in a strong decrease of the steady state concentration of the fusion and, consequently, in a null phenotype for the protein or peptide of interest.

Another aspect of the subject invention relates to methods for inhibiting the degradation of a protein bearing a degradation signal, or degron (Varshavsky, *Cell* 64: 13 (1992); Hershko & Ciechanover, *Ann. Rev. Biochem.* 61: 761 (1992)). As discussed above, the best understood intracellular degradation signal is called the N-degron. In addition to the N-degron, other amino acid sequences that function as degradation signals (and are transplantable to other proteins) include, for example, the "destruction boxes" of short-lived proteins called cyclins (Glotzer et al., *Nature* 349: 132 (1991); Ciechanover, *Cell* 79: 13, 1994)) and two specific regions of Matα2, the short-lived transcriptional regulator *S. cerevisiae* (Hochstrasser and Varshavsky, *Cell* 61: 697 (1990)).

In the experiments described in Example 2 below, it is demonstrated that the proteasome-based N-end rule pathway is remarkably sensitive to alterations in the conformational stability of its substrates. These results indicate that the degradation of a protein bearing an N-degron can be inhibited by prebinding the protein with a low molecular mass ligand (e.g., methotrexate, trimethoprim, etc.) which binds to the protein with high affinity. As used herein, a ligand having a high binding affinity is a ligand having a $K_d$ (dissociation constant) of about $10^{-8}$ or lower.

EXAMPLES

Example 1

A conditional mutant retains the function of a gene under one set of conditions, called permissive, but lacks that function under a different set of conditions, called nonpermissive; the latter must still be permissive for the wild-type allele of the gene. Conditional mutants are presumed, in most cases, to result from missense mutations in a structural gene encoding a protein. In the case of temperature-sensitive (ts) mutants, the amino acid replacement resulting from the missense mutation partially destabilizes the encoded protein, resulting in the maintenance of its three-dimensional integrity only at relatively low temperatures.

Conditional mutants make possible the analysis of physiological changes caused by inactivation of a gene or gene product, and can be used to address the function of any gene. This strategy is especially valuable for the analysis of essential genes. Several types of conditional mutants and methods for producing them have been developed since the original demonstration of the utility of ts mutants (Horowitz, *Genetics* 33, 612 (1948); Horowitz, *Adv. Genetics* 3, 33 (1950)) but the ts phenotype is still the one most frequently used.

One limitation of the ts approach is the uncertainty as to whether a given gene can be mutated to yield a ts product. For example, only six loci were identified after repeated searches for ts lethal mutations mapping to the *S. cerevisiae* chromosome I, which contains at least one hundred genes (more that six of which are essential) (Kaback et al., *Genetics* 108: 67 (1984); Harris and Pringle, *Genetics* 127: 279 (1991)). Another problem with conventional ts mutations is that they are often too "leaky" to be useful. That is, the function of a leaky ts protein at nonpermissive temperatures is not fully blocked by the mutation. For these and other reasons, a method for producing ts mutants which does not require a search for a ts mutation in a gene of interest would be extremely useful in a variety of applications.

To this end, thermolabile protein was constructed that functions as a substrate of the N-end rule pathway only at a temperature high enough to be useful as a nonpermissive temperature. This unfolding activates a previously cryptic N-degron module in the protein. Since proteolysis by the N-end rule pathway is highly processive, any protein of interest can be made conditionally short-lived by expressing it as a fusion to the thus engineered thermolabile protein, with the latter serving as a portable, heat-inducible N-degron module.

Arg-DHFR, a variant of the 21-kd mouse dihydrofolate reductase in which the wild-type N-terminal Val is replaced by Arg, is long-lived in the yeast *S. cerevisiae* ($t_{1/2}$>6 hr at 30° C.), even though Arg (unlike Val) is a destabilizing residue in the N-end rule. A search was conducted for a ts allele of Arg-DHFR whose cryptic N-degron would be activated at 37° C. but not at 23° C. A plasmid (pPW17R) was constructed that expressed Ub-Arg-DHFR-ha-Ura3 in *S. cerevisiae*.

Briefly, referring to FIG. 1, a fusion protein on the left contains an N-terminal ubiquitin (Ub) moiety, a ts dihydrofolate reductase (DHFR$^{ts}$) moiety, with a destabilizing residue such as Arg (R) at the Ub-DHFR junction, and a test protein moiety at the C-terminus of the fusion. In the experiments described herein, the test proteins were Ura3 and Cdc28 of *S. cerevisiae*. Some of the Lys (K) residues of DHFR$^{ts}$ are indicated in FIG. 1 as well. Expression of this fusion in a eukaryote such as the yeast *S. cerevisiae* results in rapid cleavage at the Ub-DHFR junction and the exposure of a destabilizing Arg (R) residue at the N-terminus of a deubiquitinated fusion. At permissive temperature (23° C.), the N-degron module of the Arg-DHFR$^{ts}$ moiety is inactive. However, at nonpermissive temperature (37° C.), a conformational destabilization of Arg-DHFR$^{ts}$ results in at least some of its lysines becoming available as ubiquitination sites of the previously cryptic N-degron module. The processive degradation of the fusion by the N-end rule pathway then ensues, greatly reducing its level in the cell. In the examples shown, the yeast Ura3 (orotidine-5'-phosphate decarboxylase) as the C-terminal moiety of the fusion resulted in Ura$^+$ cells at 23° C. but in Ura$^-$ cells at 37° C. Similarly, when the essential kinase Cdc28 was expressed as an Arg-DHFR$^{ts}$-Cdc28 fusion, cells grew at 23° C., but not at 37° C. With either Arg-DHFR$^{ts}$-Ura3 or Arg-DHFR$^{ts}$-Cdc28, the absence of the N-end rule pathway (in ubr1Δ0 cells) precluded these conditional phenotypes at 37° C. Thus, Arg-DHFR$^{ts}$ can be used as a portable, heat-inducible N-degron that yields ts mutants of a new class, called td (temperature-inducible degron).

More specifically, the CEN6, HIS3-based plasmid pPW17R, which expressed Ub-Arg-DHFR-ha-Ura3 from the *S. cerevisiae* $P_{CUP1}$ promoter, was constructed in the background of pRS313 (R. S. Sikorski and P. Hieter, *Genetics* 122, 19 (1989)). Briefly, a ~0.4 kb fragment from pJDC22-2 (K. Madura, R. J. Dohmen, A. Varshavsky, *J. Biol. Chem.* 268, 12046 (1993)) that contained the $P_{CUP1}$ promoter was ligated to a separately constructed fragment encoding Ub-Arg-DHFR-ha-Ura3. The DHFR moiety was followed by a 14-residue, ha epitope-containing sequence. The Ura3 moiety of Ub-Arg-DHFR-ha-Ura3 was actually a fusion of the last 91 residues of *S. cerevisiae* His4 to residue 6 of the Ura3 protein (E. Alani and N. Kleckner, *Genetics* 117, 5 (1987)). The ubiquitin (Ub) moiety of this fusion protein was required for production of the desired residue, such as Arg, at the N-terminus of the DHFR moiety. Ubiquitin fusions are rapidly cleaved in vivo after the last residue of ubiquitin, making possible the production of otherwise identical proteins bearing different N-terminal residues (FIG. 1) (see e.g., Varshavsky, *Cell* 69, 725 (1992)). The "ha" epitope allowed immunoprecipitation of the Arg-DHFR-ha-Ura3 fusion with a monoclonal anti-ha antibody. The *S. cerevisiae* Ura3 moiety made possible selections for or against the fusion's presence in cells, while also serving as a test protein (FIG. 1).

Purified pPW17R was mutagenized with hydroxylamine (S. Busby, M. Irani, B. deCrombrugghe, *J. Mol. Biol.* 154, 197 (1982)). The resulting DNA was used to transform the Ura$^-$ (pyrF) *E. coli* MC1066 (M. J. Casadaban, A. Martinez-Ariaz, S. K. Shapira, J. Chow, *Methods Enzymol.* 100, 293 (1983)) to ampicillin (amp) resistance, with selection on Luria Broth/amp plates at 37° C. Transformants were replica-plated onto M9 plates containing amp, Trp and Leu, and lacking uracil. The yeast URA3 gene complements the Ura$^-$ phenotype of *E.coli* pyrF mutants (M. Rose, P. Grisafi, D. Botstein, *Gene* 29, 113 (1984)). This *E. coli* screen eliminated mutant plasmids that did not express a functional Ura3 moiety of Ub-Arg-DHFR-ha-Ura3 at 37° C. However, those (potentially relevant) plasmids that expressed a mutant DHFR moiety were expected to pass this test since *E. coli* lacks the ubiquitin system. The N-terminal ubiquitin moiety of Ub-Arg-DHFR-ha-Ura3 was therefore retained in *E. coli*, precluding the formation of an N-degron.

A screen was carried out for derivatives of pPW17R that could confer onto Ura$^-$ cells a ts Ura$^+$ phenotype whose ts aspect required the N-end rule pathway. More specifically, plasmids that passed the *E. coli* screen described above were introduced in *S. cerevisiae* YPH500 (ura3), (R. S. Sikorski and P. Hieter, *Genetics* 122, 19 (1989)), with transformants selected at 23° C. on SD(-Ura) plates containing 0.1 mM CuSO$_4$. The colonies were replica-plated onto SD plates lacking His and containing 5-fluoroorotic acid (FOA) and uracil (J. D. Boeke, F. Lacroute, G. R. Fink, Mol. Gen. Genet. 197, 345 (1984)). The FOA plates were incubated at 37° C. to select against cells (carrying pPW17R plasmids) that could yield a functional Ura3 at 37° C. After several rounds of the FOA-mediated selection against cells that were Ura⁺ at 37° C., the ts URA⁺ phenotype of surviving cell clones was verified by replica-plating them onto SD(-Ura, -His) plates at 37° C. Plasmids from cells that passed these screens were introduced into the YPH500-derived strain JD15 (ubr1-Δ1::LEU2 ura3, produced identically to ubr1Δ strains described previously (B. Bartel, I. Wunning, A. Varshavsky, EMBO J. 9, 3179 (1990); K. Madura, R. J. Dohmen, A. Varshavsky, J. Biol. Chem. 268, 12046 (1993)), with transformants selected on SD(-Ura) plates at 37° C. This step narrowed the selection to plasmids whose ability to confer the ts Ura⁺ phenotype required the presence of the N-end rule pathway.

This screen yielded two mutant plasmids with the desired properties: at 23° C., these plasmids conferred a Ura⁺ phenotype, whereas at 37° C. they conferred a Ura⁻ phenotype in [UBR1 ura3] cells but a Ura⁺ phenotype in congenic [ubr1Δura3] cells. The [ubr1Δ ura3] strain lacked the N-end rule pathway because it lacked N-recognin (encoded by UBR1), the recognition component of the degradation pathway. The relevant change in both plasmids was a single missense mutation that replaced Pro with Leu at position 66 in the DHFR moiety of Ub-Arg-DHFR-ha-Ura3, yielding Ub-Arg-DHFR$^{ts}$-ha-Ura3. The Pro$^{66}$ region of DHFR connects its αII helix to the ΔC strand (C. Oefner, A. D'Arcy, F. K. Winkler, Eur. J. Biochem. 174, 377 (1988); K. W. Volz et al., J. Biol. Chem. 257, 2528 (1982)). The final construct, termed pPW43R, was produced from the unmutagenized pPW17R by replacing its EcoRI fragment encoding Ub-Arg-DHFR-ha-Ura3 with the otherwise identical fragment from one of the above plasmids encoding Ub-Arg-DHFR$^{ts}$-ha-Ura3.

Arg-DHFR$^{ts}$ was then used to produce a ts version of the S. cerevisiae Cdc28 protein kinase—an essential component of the cell cycle oscillator. The chromosomal CDC28 gene was replaced with a gene that expressed Ub-Arg-DHFR$^{ts}$-ha-Cdc28. More specifically, the plasmid pPW66R was constructed in the background of the integration vector pRS306, (R. S. Sikorski and P. Hieter, Genetics 122, 19 (1989)). Briefly, the previously described DNA fragment encoding Ub-Arg-DHFR$^{ts}$-ha was ligated to a fragment (produced using PCR and S. cerevisiae genomic DNA) that encompassed the first 284 nucleotides of the CDC28 ORF (S. I. Reed, Annu. Rev. Cell Biol. 8, 529 (1992); A. Murray, Nature 359, 599 (1992); A. B. Futcher, Semi. Cell Biol. 2, 205 (1991); K. Nasmyth, L. Dirick, U. Surana, A. Amon, F. Cvrckova, Cold Spring Harbor Symp. Quant. Biol. 56, 9 (1991); P. Nurse, Nature 344, 503 (1990)). The resulting fragment, encoding Ub-Arg-DHFR$^{ts}$-ha-Cdc28$_{1-95}$, was positioned downstream from the P$_{CUP1}$ promoter in pRS306, yielding pPW66R. This plasmid was linearized at the Msc I site (nucleotide 92 in the CDC28 ORF) and transformed into S. cerevisiae YPH500. In the resulting Ura⁺ integrants, homologous recombinations (R. Rothstein, Methods Enzymol. 194, 281 (1991)) between the proximal regions of CDC28 in pPW66R and in Chromosome II resulted in the integration of pPW66R and formation of an ORF encoding Ub-Arg-DHFR$^{ts}$-ha-Cdc28 (which contained the full-length CDC28$_{1-299}$ moiety), in addition to a nearby sequence encoding Cdc28$_{1-95}$. This truncated allele of CDC28 was neither functional nor dominant negative.

The resulting S. cerevisiae strains were compared to the wild-type (CDC28) strain YPH500. Whereas the wild-type strain grew at both 23° C. and 37° C., a representative strain expressing Ub-Arg-DHFR$^{ts}$-ha-Cdc28 (instead of the wild-type Cdc28) grew at 23° C. but was inviable at 37° C. The morphology of these cells was examined following the temperature upshift in liquid culture. After 2 hr at 37° C., cells that expressed Ub-Arg-DHFR$^{ts}$-ha-Cdc28 became larger but lacked buds (G1 phase morphology); however, by 4 hr at 37° C., many of these cells developed abnormal (elongated) buds and arrested in this configuration, which is similar to the arrest phenotype observed with some of the conventional ts alleles of CDC28. This Cdc28-mediated ts lethal phenotype required the presence of the N-end rule pathway, inasmuch as ubria cells that expressed Ub-Arg-DHFR$^{ts}$-ha -Cdc28 grew at both 23° C. and 37° C., and remained morphologically normal at 37° C.

Pulse-chase experiments confirmed that Arg-DHFR$^{ts}$-ha-Cdc28 was long-lived at 23° C. but short-lived at 27° C. ($t_{1/2} < 10$ min). More specifically, exponential cultures of either UBR1 or ubr1Δ S. cerevisiae that expressed Arg-DHFR$^{ts}$-ha-Cdc28$^{td}$, were labeled with $^{35}$S-methionine for 5 min at 23° C., followed by a chase at 23° C. or 37° C. for zero, 10 and 30 min, extraction, immunoprecipitation with anti-ha antibody, and SDS-PAGE analysis. The onset of metabolic instability of Arg-DHFR$^{ts}$-ha-Cdc28 upon the temperature upshift was extremely rapid. As could be expected from the results of phenotypic analysis, Arg-DHFR$^{ts}$-ha-Cdc28 was long-lived at both temperatures in ubriA cells which lacked the N-end rule pathway.

In addition, it was found that the addition of a specific DHFR ligand, methotrexate (MTX), to cells whose essential Cdc28 protein is expressed as the ts degron-bearing fusion (Ub-Arg-DHFR$^{ts}$-ha-Cdc28) resulted in the inhibition of heat induction of the ts N-degron upon transfer of cells to nonpermissive (N-degron-inducing) temperature. Specifically, cells expressing Ub-Arg-DHFR$^{ts}$-ha-Cdc28 remained viable at 37° C. in the presence of MTX at a sufficiently high concentration in the medium, whereas in the absence of MTX at 37° C. these cells ceased division and died, as described above. Pulse-chase experiments confirmed that this viability-rescuing effect of MTX (which is known to bind DHFR tightly and specifically) was due to the inhibition of degradation of Ub-Arg-DHFR$^{ts}$-ha-Cdc28 at 37° C. as a result of binding of MTX to DHFR.

This discovery indicated that the activity of an N-degron can also be modulated by agents other than temperature, making possible new classes of conditional mutants. Specifically, these results identified MTX as an agent that inhibits the activity of the N-degron based on the MTX ligand DHFR. They also pointed out the way to identify other such agents for N-degrons other than those based on DHFR. Specifically, these results indicated that the binding of a low molecular weight ligand to a protein component of an N-degron can interfere with the unfolding of this protein module at nonpermissive temperatures, and thereby can interfere with the targeting of the said degron by the corresponding proteolytic pathway such as the N-end rule pathway.

Example 2

Materials and Methods

The plasmids pEJJ1-R and pEJJ1-M expressed, respectively, Ub-Arg-e$^K$-DHFRha and Ub-Met-e$^K$-DHFRha (FIG. 2) from the T7 polymerase promoter in E. coli, and were constructed using the three-part ligation strategy described as follows. (i) The pT7-7 vector (Tabor and Richardson, Proc. Natl. Acad. Sci. USA 82: 1074 (1985)) was digested with NdeI and HindIII, and the larger fragment was purified by agarose gel electrophoresis, yielding the first of three fragments to be ligated. (ii) A fragment encoding the Ub-Arg/Met portions of the above fusions was produced from the plasmid pLG-Ub-M-DHFR (Bachmair and Varshavsky, Cell 56: 1019 (1989)) using PCR (Ausubel et al., Current Protocols in Molecular Biology (1992)) and the primer 5'-GAATTCCATATGCAGATTTTCGTGAAGAC-3' (the underlined sequence is the NdeI site, whose ATG is the start codon of the UB14 gene (Özkaynak et al., EMBO J. 6: 1429 (1987)). The 3' primer for this PCR encompassed the BglII site near the junction between sequences encoding the $e^K$ extension (FIG. 2) and DHFR. (iii) The third fragment to be ligated, encoding $e^K$-DHFRha, was a ~600 bp BamHI-HindIII fragment derived from pLG-Ub-M-DHFRha (Johnson, Ph.D. Thesis, Massachusetts Institute of Technology, Cambridge, Mass. (1992)). The sequence of DHFR-linked $e^K$ differed from that of the βgal-linked $e^K$ near the $e^K$-reporter junction. Ligation of these three fragments (the second one encoding either Arg or Met at the Ub-$e^K$ junction) yielded a pEJJ1-R and pEJJ1-M, encoding, respectively, Ub-Arg-$e^K$-DHFRha and Ub-Met-$e^K$-DHFRha. The plasmids pPJJ1-R and pPJJ1-M, expressing, respectively, Ub-Arg-Δe-DHFRha and Ub-Met-Δe-DHFRha (FIG. 2) were produced from pEJJ1-R and pEJJ1-M. The BamHI-HindIII fragment (encoding $e^K$-DHFRha) was excised from the latter plasmids and replaced with a ~600 bp fragment of pPW17-R (Dohmen et al., Science 263: 1273 (1994)) that encoded Arg-His-Gly-Ser-Gly-Ile-Met-DHFRha.

E. coli JM101 and DH5α' (Ausubel et al., Current Protocols in Molecular Biology (1992)) were used as hosts in plasmid construction and in plasmid preparation for sequencing, respectively. The final constructs were verified by restriction mapping and nucleotide sequencing. E. coli BL21 (DE3) (Studier and Moffat, J. Mol. Biol. 189: 113 (1986)) was used for overexpression of DHFR-containing fusions.

Unless stated otherwise, all procedures were carried out at 4° C. 0.5 ml of an overnight culture of E. coli BL21 (DE3) carrying one of the pT7-based plasmids was diluted into 50 ml of Luria Broth (LB) containing ampicillin (Amp) at 75 µg/ml, and the culture was grown at 37° C. to $A_{600}$ of ~0.2; more Amp was then added, to a final concentration of 115 µg/ml, and the incubation was continued until $A_{600}$ of ~0.6 was reached. Isopropylthiogalactoside (IPTG) was then added to a final concentration of 0.2 mM. The culture was grown for another 25 min at 30° C.; the cells were harvested by centrifugation at 4,000 g for 10 min, washed twice with M9 buffer resuspended in 1 ml of M9 supplemented with 0.22% glucose, rifampicin (0.2 mg/ml), Amp (75 µg/ml) and 0.1% Methionine Assay Medium (Difco), and incubated with 0.5 mCi of $^{35}$S-Translabel (ICN) for 10 min at 30° C. The cells were collected by centrifugation, washed once with LB, twice with M9 buffer, and resuspended in 0.5 ml of 25% (w/v) sucrose, 50 mM Tris-HCl, pH 8.0. 0.1 ml of a lysozyme solution (10 mg/ml in 0.25M Tris-HCl, pH 8.0) was then added. After 5 min at room temperature, 0.8 ml of the lysis buffer (1% Triton X-100, 37 mM Na-EDTA, 50 mM Tris-HCl, pH 8.0) was added, and the suspension was vortexed for 10 sec twice, followed by a quick freezing in liquid $N_2$ and thawing of the sample in a 37° water bath. The lysate was centrifuged at 40,000 g for 25 min, and Ub-X-DHFRha (this term denotes both Ub-X-$e^K$-DHFRha and Ub-X-Δe-DHFRha; FIG. 2) in the supernatant was bound to the monoclonal anti-ha antibody 12CA5 (Field et al., Mol. Cell. Biol. 8: 2159 (1988); Johnson et al., EMBO J. 11: 497 (1992)), added as an ascitic fluid, in a roughly 100-fold molar excess over Ub-X-DHFRha. The antibody-bound Ub-X-DHFRha was immobilized on a 0.5-ml column of Protein A-Sepharose (Repligen, Cambridge, Mass.). The column was washed with 5 ml of 10 mM Na-phosphate buffer (pH 7.5). Ub-X-DHFRha was eluted with 2.5M LiCl in the same buffer. The sample was dialyzed overnight against 50 mM Tris-HCl (pH 7.5), then concentrated by dialysis for ~20 hr against 50% (v/v) glycerol, 0.1 mM EDTA, 1 mM dithiothreitol (DTT), 1 mM $MgCl_2$, 50 mM Tris-HCl (pH 7.5), and stored at −20° C. The specific radioactivity of $^{35}$S-labeled Ub-X-DHFRha was ~$10^4$ cpm/µg. Protein concentrations were determined using the Bradford (Coomassie Blue) Assay (Pierce; Rockford, Ill.). Ub-DHFR fusions purified as described above were conformationally unperturbed in that they could be retained on an MTX-Sepharose column (Pierce).

Rabbit reticulocytes were purchased from Green Hectares (Oregon, Wis.) and shipped overnight on ice. ATP-depleted reticulocyte extract was prepared as described by Gonda et al., J. Biol. Chem 264: 16700 (1989), and stored as 0.2-ml samples in liquid $N_2$. Only once-frozen samples were used in all experiments. An assay mixture contained 75 µl of the extract, 10 µl of an $^{35}$S-labeled Ub-X-DHFRha, 0.1 mM DTT, 5 mm $Mgcl_2$, 0.8 mM ATP and an ATP-regenerating system (10 mM creatine phosphate, 0.1 mg/ml creatine phosphokinase). Assays were performed as follows. A reaction mixture complete except for ATP and ATP-regenerating system was incubated for 10 min at 37° C. to allow for the deubiquitination of a Ub-X-DHFRha fusion protein; an aliquot was then withdrawn (time zero in FIG. 3). ATP and ATP-regenerating system were added to start ATP-dependent reactions in the extract, and the incubation continued at 37° C.

The initial concentration of an $^{35}$S-labeled Ub-X-DHFRha in the extract was ~5 µg/ml; control experiments indicated that this concentration was not rate-limiting for the degradation of either Arg-$e^K$-DHFRha or Arg-Δe-DHFRha. MTX (where indicated) was added from a 2M stock solution in 0.2M NaOH to Ub-X-DHFRha in a reaction tube and incubated for 5 min at 0° C. before assembling the reaction mixture as described above. The final MTX concentration was 20 µM. Two equal samples were withdrawn from reaction tubes at the times indicated in FIG. 3. One sample was assayed for the amount of 5% trichloroacetic acid (TCA)-soluble $^{35}$S, and the other was examined by a Tricine buffer-based SDS-PAGE (9% acrylamide, 0.24% bisacrylamide) (Schagger and Jagow, Anal. Biochem. 166: 368 (1987)). The gels were analyzed using fluorography on a PhosphorImager (Molecular Dynamics, Sunnyvale, Calif.). TCA-soluble $^{35}$S was determined as follows: 0.1 ml of a solution of bovine serum albumin (50 mg/ml) was added to a 10-µl sample; 0.11 ml of 10% TCA was then added; the sample was incubated on ice for 10 min, followed by centrifugation at 12,000 g for 5 min. $^{35}$S in the supernatant was determined using a water-compatible scintillation cocktail and a scintillation counter. In each of the graphs of FIG. 3, the amount of TCA-soluble $^{35}$S in a zero-point sample (before the addition of ATP; 5–10% of total $^{35}$S) was subtracted from the values for samples withdrawn at later times.

Results

Linear Ub fusions are rapidly cleaved in vivo or in cell-free extracts after the last residue of Ub, making possible the production of otherwise identical proteins bearing different N-terminal residues. In one application of this method, fusions of Ub to E. coli β-galactosidase (Ub-X-βgals) were incubated in reticulocyte extract, producing X-βgal test proteins bearing different N-terminal residues.

Depending on the identity of a residue X, an X-βgal is either short-lived or metabolically stable in ATP-supplemented extract, similarly to the in vivo findings with the same X-βgals in the yeast *Saccharomyces cerevisiae* (Bachmair et al., *Science* 234: 179 (1986)). Mutational analysis has shown that either one of two lysines (Lys-15 or Lys-17) in a non-βgal N-terminal region of an X-βgal test protein was also required for rapid degradation of X-βgal by the N-end rule pathway (FIG. 2). The function of these lysines was identified by the finding that Lys-15 or, alternatively, Lys-17 is the site of formation of a multi-Ub chain. The non-βgal, ~40-residue extension at the N-terminus of βgal was derived in part from an internal sequence of *E. coli* Lac repressor (Bachmair and Varshavsky, *Cell* 56: 1019 (1989)).

In the present Example, the strategy used by Gonda et al., *J. Biol. Chem* 264: 16700 (1989) with βgal-based substrates was employed to examine the degradation of similarly designed DHFR-based substrates by the N-end rule pathway in reticulocyte extract. The ~40-residue N-terminal extension of DHFR, derived from X-βgal test proteins (FIG. 2) (Bachmair and Varshavsky, *Cell* 56: 1019 (1989)), is denoted below as $e^K$ [extension (e) containing lysine (K)] (Johnson et al., *EMBO J.* 11: 497 (1992)). In the constructs of FIG. 2, the C-terminus of Ub-X-$e^K$-DHFR was extended with a 14-residue sequence containing "ha", an epitope tag derived from the influenza virus hemagglutinin that could be recognized by a monoclonal antibody (Field et al., *Mol. Cell. Biol.* 8: 2159 (1988); Johnson et al., *EMBO J.* 11: 497 (1992)). Two fusion proteins, Ub-Met-$e^K$-DHFRha and Ub-Arg-$e^K$-DHFRha (FIG. 2), bore, respectively, Met and Arg—a stabilizing and a destabilizing residue at the junction between Ub and the rest of a fusion (Varshavsky, *Cell* 69: 725 (1992)). These proteins were overexpressed in *E. coli*, labeled in vivo with $^{35}$S-methionine, and purified by affinity chromatography, using anti-ha antibody.

Ub-Met-$e^K$-DHFRha and Ub-Arg-$e^K$-DHFRha were rapidly deubiquitinated upon addition to ATP-depleted reticulocyte extract, yielding, respectively, Met-$e^K$-DHFRha and Arg-$e^K$-DHFRha, analogous to the previously characterized deubiquitination of Ub-X-$e^K$-βgal fusions under the same conditions (Gonda et al., *J. Biol. Chem* 264: 16700 (1989)).

Figure 3B:
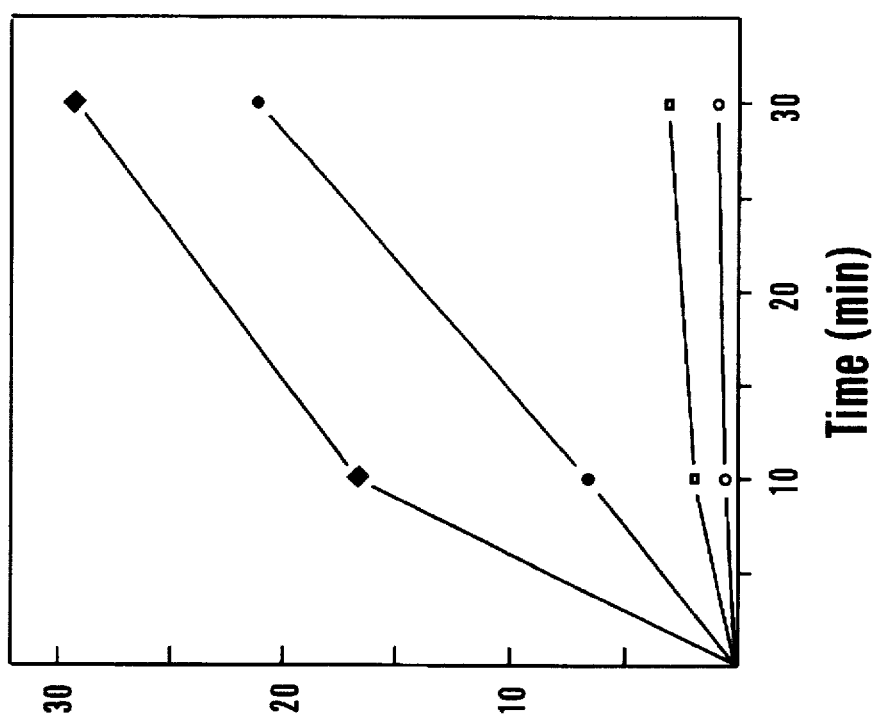
FIG. 3 is a diagram representing degradation studies of DHFR-based N-end rule substrates in reticulocyte extract, measured by determining acid-soluble $^{35}$S. (A) -□-, Met-$e^K$-DHFRha; -♦-, Arg-$e^K$-DHFRha; -X -, Arg-$e^K$-DHFRha in the presence of 1 mM Arg-Ala depeptide; -◊-, Arg-$e^K$-DHFRha in the presence of 20 μM methotrexate. (B) -□-, same as in A but from another experiment with Met-$e^K$-DHFRha; -♦-, Arg-$e^K$-DHFRha; -●-, Arg-Δe-DHFRha; -○-, Arg-Δe-DHFRha in the presence of 20 μM methotrexate. Each decay curve was determined at least thrice, in independent experiments, with the results differing by less than 15% for each of the time points.
Figure 3A:
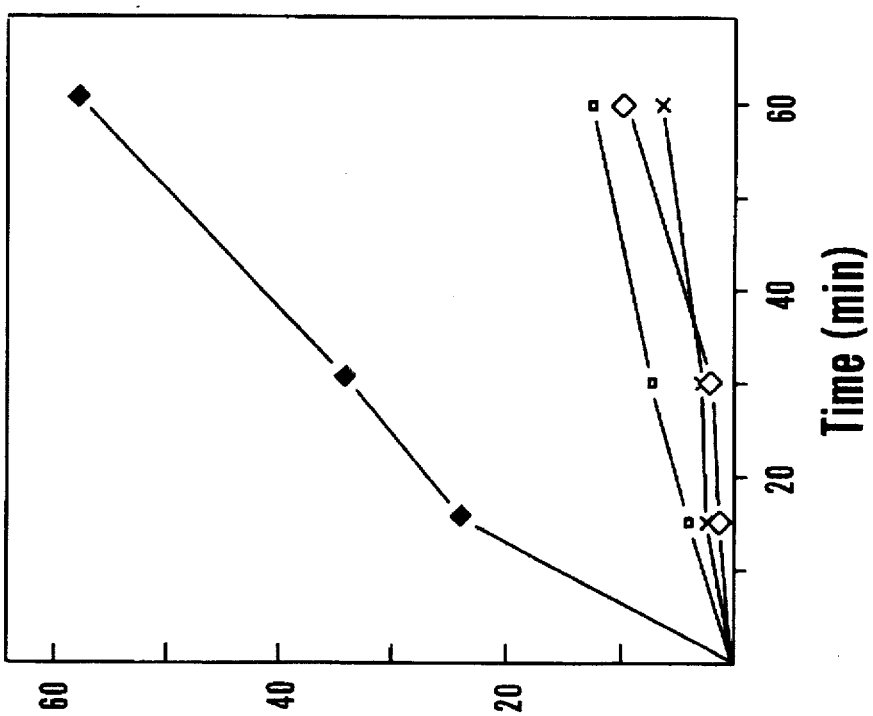

Both Met-$e^K$-DHFRha and Arg-$e^K$-DHFRha remained metabolically stable in ATP-depleted extract, but the addition of ATP resulted in a much faster degradation of Arg-$e^K$-DHFRha than Met-$e^K$-DHFRha, which remained long-lived in ATP-supplemented extract (FIG. 3A). The metabolic fates of DHFR-based test proteins were monitored by SDS-PAGE, and also by measuring the amount of acid soluble $^{35}$S released during the incubation of an $^{35}$S-labeled protein in ATP-supplemented extract (FIG. 3).

As shown in FIG. 3A, 33% of the initially present $^{35}$S-labeled Arg-$e^K$-DHFRha was degraded to acid-soluble fragments in ATP-supplemented reticulocyte extract after a 30-min incubation. By contrast, only about 6% of the otherwise identical Met-$e^K$-DHFRha, bearing an N-terminal Met (stabilizing residue in the N-end rule), was degraded after a 30 min incubation (FIG. 3A). Analysis by SDS-PAGE showed a transient accumulation of multiply ubiquitinated Arg-$e^K$-DHFRha derivatives and a decrease in intensity of the band of unmodified Arg-$e^K$-DHFRha in the course of its incubation in ATP-supplemented extract. By contrast, Met-$e^K$-DHFRha was neither ubiquitinated nor significantly degraded in ATP-supplemented extract, in agreement with the findings about similarly designed X-βgal substrates (Gonda et al., *J. Biol. Chem* 264: 16700 (1989)).

Previous work has shown that an amino acid derivative such as a dipeptide that bears a destabilizing N-terminal residue can inhibit the degradation of a βgal-based N-end rule substrate either in vitro (reticulocyte extract) or in vivo (yeast cells). The degradation of a DHFR-based N-end rule substrate such as Arg-$e^K$-DHFRha in reticulocyte extract was almost completely inhibited by the Arg-Ala dipeptide. Dipeptides bearing destabilizing N-terminal residues inhibit the N-end rule pathway by competing with N-end rule substrates for binding to N-recognin. Arg-Ala not only precluded the degradation of Arg-$e^K$-DHFRha (FIG. 3A) but also inhibited its deubiquitination, indicating that Arg-Ala blocks a step in the N-end rule pathway that precedes the ubiquitination step.

It was then tested whether the folate analog methotrexate (MTX)—a high-affinity DHFR ligand ($K_d$ of ~$10^{-11}$M) and a competitive inhibitor of DHFR (Matthews et al., *J. Biol. Chem.* 260: 392 (1985)) would affect the degradation of a DHFR-based N-end rule substrate. Remarkably, the presence of MTX in ATP-supplemented reticulocyte extract resulted in a nearly complete inhibition of Arg-$e^K$-DHFRha degradation (FIG. 3A). The inhibitory effect of MTX was confined to the actual proteolysis of Arg-$e^K$-DHFRha: its multiubiquitination was, in fact, enhanced by MTX, in contrast to the effect of Arg-Ala, which inhibited both the degradation and ubiquitination of Arg-$e^K$-DHFRha.

The effect of MTX on degradation of Arg-Δe-DHFRha (derived from Ub-Arg-Δe-DHFRha), which lacked most of the ~40 residue, lysine-containing eK extension of Arg-$e^K$-DHFRha (FIG. 2) was also determined. Previous work has shown that Arg-Δe-DHFRha is much longer-lived than Arg-$e^K$-DHFRha in the yeast *S. cerevisiae* at 30° C. ($T_{1/2}$ of more than 4 hr versus ~10 min, respectively); it has also been shown that a major reason for the increased metabolic stability of Arg-Δe-DHFRha is the absence of Lys-15, 17: Arg-$e^{\Delta K}$-DHFRha, which contains Arg instead of Lys at positions 15 and 17 of the otherwise unaltered $e^K$ extension, is nearly as long-lived in yeast as Arg-Δe-DHFRha. In qualitative agreement with these in vivo data, Arg-Δe-DHFRha was degraded more slowly than Arg-$e^K$-DHFRha in ATP-supplemented reticulocyte extract (FIG. 3B). The degradation of Arg-Δe-DHFRha was mediated by the N-end rule pathway, inasmuch as Met-Δe-DHFRha, bearing a stabilizing N-terminal residue, was degraded at a much slower rate than Arg-Δe-DHFRha.

Similarly to the findings with Arg-$e^K$-DHFRha, the addition of MTX almost completely inhibited the degradation of Arg-Δe-DHFRha in ATP-supplemented extract (FIG. 3B). In contrast to the extensive ubiquitination of Arg-$e^K$-DHFRha prior to its degradation, the degradation of Arg-Δe-DHFRha was not accompanied by a significant accumulation of its multiubiquitinated derivatives.

The effect of MTX was confined to DHFR-based substrates: in parallel assays with βgal-based N-end rule substrates such as Arg-$e^K$-βgal, the addition of MTX did not alter the kinetics of Arg-$e^K$-βgal degradation. In sum, these experiments revealed a strong and specific inhibition of the degradation of a degron-bearing protein such as DHFR by a low molecular mass, tightly binding ligand such as methotrexate.

Figure 4:
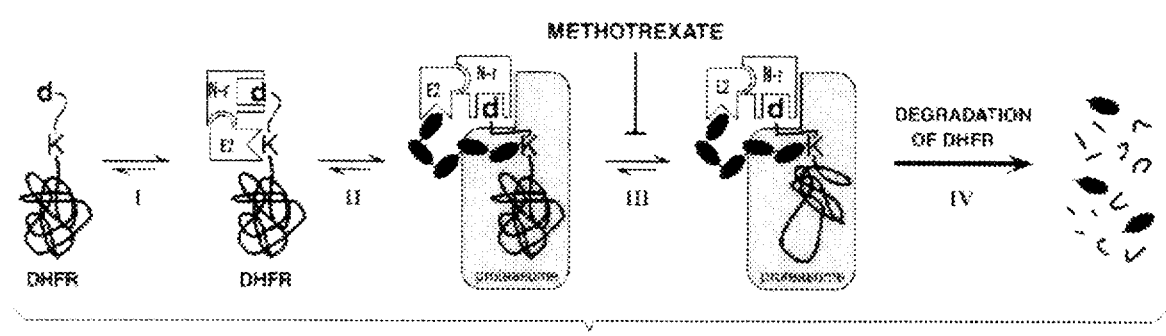
FIG. 4 is a diagram representing a proposed mechanism for the reported methotrexate effect.

While not wishing to be bound by theory, FIG. 4 depicts a mechanistic model which is consistent with the methotrexate effect observed. Each of the four depicted transitions (I–IV) in the N-end rule pathway is actually a multi-step reaction (Varshavsky, *Cell* 69: 725 1992)). The shapes of structures are arbitrary. Among the protein-protein complexes shown in this diagram, the interactions between N-recognin (N-r) and the Ub-conjugating enzyme (E2), and between N-recognin and a DHFR-based N-end rule substrate were demonstrated directly (Bartel et al., *EMBO J.* 9: 3179 (1990); Madura et al., *J. Biol. Chem.* 268: 12046 (1993)). An interaction between N-recognin and proteasome is suggested by a variety of evidence. The path of a multi-Ub chain (black ovals) in a complex between proteasome and a multiubiquitinated substrate is unknown. However, if the E2 enzyme that initiates the formation of a substrate-linked multi-Ub chain is also responsible for the chain elongation, the growing tip of the chain must be in proximity to this E2, as shown in FIG. 4. Superimposition of the substrate and proteasome denotes a complex (of unknown structure) between them. A DHFR-based N-end rule substrate such as Arg-e$^K$-DHFRha (FIG. 2), bearing a destabilizing N-terminal residue (d) and a mobile lysine residue (K) outside of the folded DHFR globule is bound by a complex of N-recognin and E2 (step I). Formation of a lysine-linked multi-Ub chain (the chain's length is arbitrarily set at five Ub moieties) and the binding of a multiubiquitinated substrate by the proteasome take place at step II. In vitro, the multiubiquitination of an N-end rule substrate can occur in the absence of proteasome; however, it is possible that the binding of a targeted substrate by the proteasome accompanies or even precedes the substrate's multiubiquitination in vivo. At step III, a local or a global conformational perturbation of DHFR in a complex with the proteasome occurs, resulting in proteolysis—the irreversible step IV, which yields short fragments of DHFR and regenerates Ub from a multi-Ub chain. Formation of the MTX-DHFR complex stabilizes the folded DHFR conformation, decreasing the probability of a conformational perturbation of DHFR (step III) that can be "utilized" by the proteasome, and thereby inhibiting the degradation of a DHFR-containing substrate. In the case of a protein such as Arg-Δe-DHFRha (FIG. 2), which lacks a targetable lysine residue outside of the DHFR globule, the binding of MTX and the resulting conformational stabilization of DHFR suppress both ubiquitination and degradation of Arg-Δe-DHFRha.

We claim:

1. A method for inhibiting the degradation of a degron-bearing protein, the method comprising:

a) providing a protein bearing the N-degron of SEQ ID NO: 2, or an N-degron including a destabilizing N-terminal amino acid residue, an internal lysine amino acid residue which functions as an attachment site for a multiubiquitin chain at a permissive temperature, but not at a non-permissive temperature in a eukaryotic cell or cell extract and is encoded by a eukaryotic DNA sequence which hybridizes under stringent conditions to the DNA sequence represented in SEQ ID NO: 1;

b) contacting the protein with a low molecular mass, cell penetrating ligand which binds to the protein with high affinity, the low molecular mass, cell penetrating ligand being selected from the group consisting of methotrexate and trimethoprim; and c) incubating the mixture of step b) under conditions which, absent the low molecular mass, cell penetrating ligand, would result in the degradation of the protein.

2. The method of claim 1 wherein the dissociation constant between the ligand and the protein is at least $10^{-8}$.

3. A method for inhibiting the degradation of a fusion protein in vitro, comprising:

a) providing a fusion protein comprising a protein of interest linked at its N-terminus to the N-degron of SEQ ID NO: 2, or an N-degron including a destabilizing N-terminal amino acid residue, an internal lysine amino acid residue which functions as an attachment site for a multiubiquitin chain at a permissive temperature, but not at a non-permissive temperature in a eukaryotic cell or cell extract and is encoded by a eukaryotic DNA sequence which hybridizes under stringent conditions to the DNA sequence represented in SEQ ID NO: 1;

b) contacting the fusion protein with methotrexate at a concentration of from about 10 μM to about 50 μM; and c) incubating the mixture of step b) under conditions which, absent methotrexate, would result in the degradation of the fusion protein.

4. A method for inhibiting the degradation of a fusion protein in a cell, comprising:

a) transforming a cell with an expression construct encoding a fusion protein comprising a protein of interest linked at its N-terminus to the N-degron of SEQ ID NO: 2, or an N-degron including a destabilizing N-terminal amino acid residue, an internal lysine amino acid residue which functions as an attachment site for a multiubiquitin chain at a permissive temperature, but not at a non-permissive temperature in a eukaryotic cell or cell extract and is encoded by a eukaryotic DNA sequence which hybridizes under stringent conditions to the DNA sequence represented in SEQ ID NO: 1;

b) contacting the cell with concentration of methotrexate sufficient to achieve an intracellular concentration of at least 10 μM; and c) incubating the mixture of step b) under conditions which, absent methotrexate, would result in degradation of the expressed fusion protein within the cell.

* * * * *